(12) United States Patent
Watanabe et al.

(10) Patent No.: US 11,191,711 B2
(45) Date of Patent: Dec. 7, 2021

(54) HAIR DYE

(71) Applicant: Shiseido Company, Ltd., Tokyo (JP)

(72) Inventors: Daisuke Watanabe, Tokyo (JP); Takanori Matsubara, Hyogo (JP); Naoka Ise, Hyogo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 17/253,461

(22) PCT Filed: Jun. 19, 2019

(86) PCT No.: PCT/JP2019/024249
§ 371 (c)(1),
(2) Date: Dec. 17, 2020

(87) PCT Pub. No.: WO2019/244919
PCT Pub. Date: Dec. 26, 2019

(65) Prior Publication Data
US 2021/0113445 A1  Apr. 22, 2021

(30) Foreign Application Priority Data
Jun. 19, 2018  (JP) .............................. JP2018-116502

(51) Int. Cl.
| | |
|---|---|
| *A61Q 5/10* | (2006.01) |
| *A61K 8/49* | (2006.01) |
| *A61K 8/19* | (2006.01) |
| *A61K 8/20* | (2006.01) |
| *A61K 8/34* | (2006.01) |
| *A61K 8/35* | (2006.01) |
| *A61K 8/44* | (2006.01) |
| *A61K 8/46* | (2006.01) |
| *A61K 8/60* | (2006.01) |

(52) U.S. Cl.
CPC ................ *A61K 8/498* (2013.01); *A61K 8/19* (2013.01); *A61K 8/20* (2013.01); *A61K 8/34* (2013.01); *A61K 8/35* (2013.01); *A61K 8/447* (2013.01); *A61K 8/46* (2013.01); *A61K 8/4973* (2013.01); *A61K 8/602* (2013.01); *A61Q 5/10* (2013.01); *A61K 2800/4322* (2013.01); *A61K 2800/4324* (2013.01); *A61K 2800/88* (2013.01)

(58) Field of Classification Search
CPC ... A61Q 5/10; A61K 8/22; A61K 8/19; A61K 8/49; A61K 2800/4324; A61K 2800/88; A61K 8/34; A61K 8/345; A61K 8/4973; A61K 8/498; A61K 8/447; A61K 2800/4322
USPC .......................................................... 8/405
See application file for complete search history.

(56) References Cited

U.S. PATENT DOCUMENTS

| 4,517,175 A | 5/1985 | Iwabuchi et al. | |
|---|---|---|---|
| 2007/0166256 A1* | 7/2007 | Shiroyama | A61K 8/9794 424/70.2 |
| 2012/0141398 A1 | 6/2012 | Chuang | |
| 2013/0266530 A1* | 10/2013 | Bhogal | A61K 8/498 424/70.1 |
| 2014/0088184 A1* | 3/2014 | Seron | A61K 45/06 514/456 |

(Continued)

FOREIGN PATENT DOCUMENTS

| JP | 59-051209 A | 3/1984 |
|---|---|---|
| JP | 2008-303181 A | 12/2008 |

(Continued)

OTHER PUBLICATIONS

STIC Search Report dated Jun. 11, 2021.*
Arai, Yasuhiro, "The Newest Hair Coloring Technology," Fragrance Journal Ltd., Aug. 2004, p. 102, with English translation.

*Primary Examiner* — Eisa B Elhilo
(74) *Attorney, Agent, or Firm* — Foley & Lardner LLP

(57) ABSTRACT

A hair dye that is safe for human bodies and has a high hair dyeing effect is provided.
The hair dye consisting of:
a reaction solution (A) comprising: a substance having a specific flavonoid skeleton represented by the following general formula (1); one type or two or more types selected from benzyl alcohol, vanillin, propylene carbonate, and γ-butyrolactone; and one type or two or more types selected from a thioglycolic acid salt, a thiolactic acid salt, cysteine and cysteamine, and
a reaction solution (B) comprising an oxidizing agent.

[Formula 1]

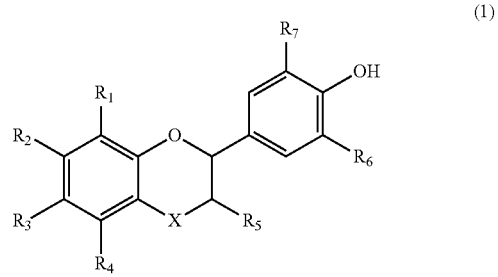

(In the formula, $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents >$CH_2$, >C=O, or >CHOH.)

10 Claims, No Drawings

(56) References Cited

U.S. PATENT DOCUMENTS

2015/0231050 A1   8/2015  Lan et al.

FOREIGN PATENT DOCUMENTS

| JP | 2012-116829 A | 6/2012 |
| JP | 2015-526449 A | 9/2015 |
| JP | 2016-008190 A | 1/2016 |
| JP | 2018-145578 A | 9/2018 |
| WO | WO-2012/084568 A1 | 6/2012 |
| WO | WO-2015/074821 A1 | 5/2015 |
| WO | WO-2015/198923 A1 | 12/2015 |

* cited by examiner

HAIR DYE

CROSS REFERENCE TO RELATED APPLICATIONS

This application is the U.S. National Stage of PCT/JP2019/024249, filed Jun. 19, 2019, which is based upon and claims the benefit of the priority of Japanese Patent Application No. 2018-116502, filed on Jun. 19, 2018, the disclosure of which is incorporated herein by reference in its entirety.

TECHNICAL FIELD

The present disclosure relates to a hair dye, and particularly to a hair dye that is safe for human bodies and has a high hair dyeing effect.

BACKGROUND ART

Oxidative hair dyes using oxidative dyes are generally called as hair coloring agents, and they are widely used as permanent dyes because of their fastness. Oxidative hair dyes usually consist of a first agent comprising an oxidative dye precursor that is oxidized inside hair and produces an oxidative dye, and a second agent comprising an oxidizing agent such as hydrogen peroxide that oxidizes the oxidative dye precursor. The first agent and the second agent are mixed upon application, and oxidative dyes are produced thereby to dye hair. Since oxidative dyes that are produced by oxidization inside hair are polymers, it is said that they are hardly desorbed from inside of hair, and thus a high fastness can be achieved (e.g. Non-Patent Literature 1).

The oxidative dye precursors used in oxidative dyes, however, are known as a representative allergen.

Accordingly, dyes that are safer for human bodies are demanded. In recent years, dyes that uses oxidants (o-quinone compounds) obtained by electro-oxidizing catechin that is a natural substance having a flavonoid skeleton are known (Patent Literature 1). However, there was a room for improvement in their dyeing effects.

CITATION LIST

Patent Literature

Patent Literature 1: Japanese Unexamined Patent Publication No. 2008-303181 A.

Non-Patent Literature

Non-Patent Literature 1: Yasuhiro ARAI, "The Newest Hair Coloring Technology", Fragrance Journal Ltd., August 2004, p. 102

SUMMARY OF INVENTION

Technical Problem

The present invention has been made in view of the above-mentioned conventional art, and an object to be solved is to provide a hair dye that is safe for human bodies and has a high hair dyeing effect.

Solution to Problem

The present inventors have diligently studied the above-mentioned problem, and as a result, they have found that a hair dye that is safe for human bodies and has a high hair dyeing effect can be obtained from a reaction solution (A) comprising: a substance having a specific flavonoid skeleton; one type or two or more types selected from benzyl alcohol, vanillin, propylene carbonate, and γ-butyrolactone; and one type or two or more types selected from a thioglycolic acid salt, a thiolactic acid salt, cysteine and cysteamine, and a reaction solution (B) comprising an oxidizing agent, and thus completed the present invention.

That is, the hair dye according to the present invention consists of:
a reaction solution (A) comprising: a substance having a specific flavonoid skeleton represented by the following general formula (1); one type or two or more types selected from benzyl alcohol, vanillin, propylene carbonate, and γ-butyrolactone; and one type or two or more types selected from a thioglycolic acid salt, a thiolactic acid salt, cysteine and cysteamine, and
a reaction solution (B) comprising an oxidizing agent.

[Formula 1]

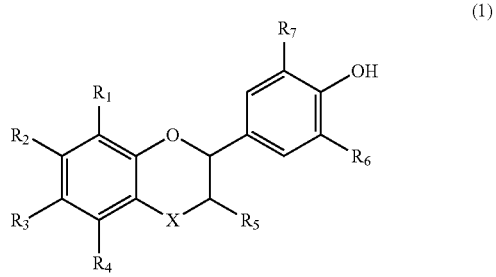

(1)

(In the formula, $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents $>CH_2$, $>C=O$, or $>CHOH$.)

In the hair dye, the oxidizing agent is preferably selected from a group consisting of a bromate, periodic acid, a periodate, hydrogen peroxide, an inorganic or organic alkali metal peroxide, a peroxy acid salt, an inorganic perhydrate salt, alkyl or aryl peroxide, peroxidase, oxidase, uricase, a percarbonate, a persulfate, and peroxo-monocarbonate.

The hair dye according to the preset invention consists of:
a reaction solution (A) comprising a substance having a flavonoid skeleton represented by the following general formula (1), and
a reaction solution (B) comprising an oxidizing agent consisting of a bromate.

[Formula 2]

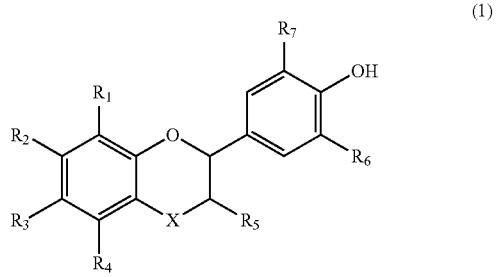

(1)

(In the formula, $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents >$CH_2$, >C=O, or >CHOH.)

In the hair dye, pH of the reaction solution (B) is preferably 7 or greater.

A hair dyeing method according to the present invention comprises steps of:

an adsorbing step of treating hair with a reaction solution (A) comprising: a substance having a flavonoid skeleton represented by the following general formula (1); one type or two or more types selected from benzyl alcohol, vanillin, propylene carbonate, and γ-butyrolactone; and one type or two or more types selected from a thioglycolic acid salt, a thiolactic acid salt, cysteine and cysteamine; and an oxidizing step of treating the hair with a reaction solution (B) comprising an oxidizing agent.

[Formula 3]

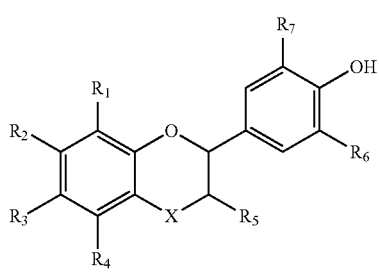

(1)

(In the formula, $R_1$, $R_2$, $R_3$, $R_4$, $R_6$, and $R_7$ independently represent a hydrogen atom, a hydroxy group, or a methyl group; either one or both of $R_6$ and $R_7$ are a hydroxy group; $R_5$ represents a hydrogen atom, a hydroxy group, a galloyl group, or a saccharide; and X represents >$CH_2$, >C=O, or >CHOH.)

In the hair dyeing method, the oxidizing agent is preferably selected from a group consisting of a bromate, periodic acid, a periodate, hydrogen peroxide, inorganic or organic alkali metal peroxide, a peroxy acid salt, an inorganic perhydrate salt, alkyl or aryl peroxide, peroxidase, oxidase, uricase, a percarbonate, a persulfate, and peroxo monocarbonate.

In the hair dyeing method, the adsorbing step is preferably a step of treating hair with a reaction solution (A-2) comprising a substance having a flavonoid skeleton represented by a general formula (1) after a pre-treatment step of treating hair with a reaction solution (A-1) comprising: one type or two or more types selected form benzyl alcohol, vanillin, propylene carbonate, and γ-butyrolactone; and one type or two or more types selected from a thioglycolic acid salt, a thiolactic acid salt, cysteine and cysteamine.

A hair dyeing method according to the present invention comprises steps of:

an adsorbing step of treating hair with a reaction solution (A) comprising a substance having a flavonoid skeleton represented by the following general formula (1); and an oxidizing step of treating the hair with a reaction solution (B) comprising an oxidizing agent consisting of a bromate.

[Formula 4]

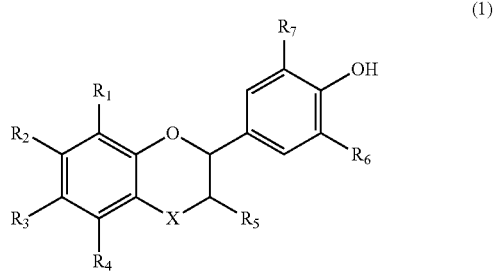

(1)

(In the formula, $R_1$, $R_2$, $R_3$, $R_4$, $R_6$, and $R_7$ independently represent a hydrogen atom, a hydroxy group, or a methyl group; either one or both of $R_6$ and $R_7$ are a hydroxy group; $R_5$ represents a hydrogen atom, a hydroxy group, a galloyl group, or a saccharide; and X represents >$CH_2$, >C=O, or >CHOH.)

In the hair dyeing method, pH of the reaction solution (B) is preferably 7 or greater.

Advantageous Effects of Invention

According to the present invention, a hair dye that is safe for human bodies and has a high hair dyeing effect can be obtained.

DESCRIPTION OF EMBODIMENTS

Hereinbelow, embodiments of the present invention are described in detail.

The hair dye according to the present invention consists of a reaction solution (A) comprising: a substance having a specific flavonoid skeleton; one type or two or more types selected from benzyl alcohol, vanillin, propylene carbonate, and γ-butyrolactone; and one type or two or more types selected from a thioglycolic acid salt, a thiolactic acid salt, cysteine and cysteamine, and a reaction solution (B) comprising an oxidizing agent.

Moreover, the hair dye according to the present invention consists of a reaction solution (A) that comprises a substance having a specific flavonoid skeleton and a reaction solution (B) that comprises an oxidizing agent consisting of a bromate.

<Reaction Solution (A)>

The substance having a flavonoid skeleton used in the hair dye according to the present invention is a compound represented by the following general formula (1).

[Formula 5]

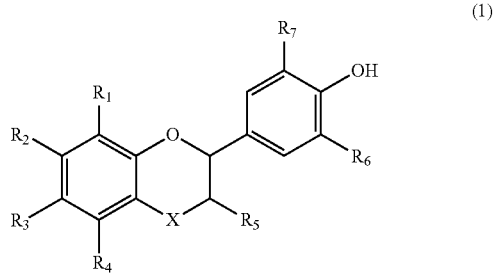

(1)

Here, $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents >$CH_2$, >C=O, or >CHOH.

Specific examples may include those that are listed below. "pyro" represents pyrogallol.

(1) (+)-Catechin or (−)-catechin or (+)-epicatechin or (−)-epicatechin
$R_1$, $R_3$, $R_6$: H; $R_2$, $R_4$, $R_5$, $R_7$: OH; X: >$CH_2$ (2) (+)-Gallocatechin or (−)-gallocatechin or (−)-epigallocatechin
$R_1$, $R_3$: H; $R_2$, $R_4$, $R_5$, $R_6$, $R_7$: OH; X: >$CH_2$ (3) (−)-Catechin gallate or (−)-epicatechin gallate
$R_1$, $R_3$, $R_6$: H; $R_2$, $R_4$, $R_7$: OH; $R_5$: O—C=O-pyro; X: >$CH_2$ (4) (−)-Gallocatechin gallate or (−)-epigallocatechin gallate
$R_1$, $R_3$: H; $R_2$, $R_4$, $R_6$, $R_7$: OH; $R_5$: O—C=O-pyro; X: >$CH_2$ (5) Taxifolin
$R_1$, $R_3$, $R_6$: H; $R_2$, $R_4$, $R_5$, $R_7$: OH; X: >C=O (6) Fuscin
$R_1$, $R_3$, $R_4$, $R_6$: H; $R_2$, $R_5$, $R_7$: OH; X: >C=O (7) Luteolin
$R_1$, $R_3$, $R_5$, $R_6$: H; $R_2$, $R_4$, $R_7$: OH; X: >C=O; flavone structure (8) 6-Hydroxyluteolin
$R_1$, $R_5$, $R_6$: H; $R_2$, $R_3$, $R_4$, $R_7$: OH; X: >C=O; flavone structure (9) 6-Methoxyluteolin
$R_1$, $R_5$, $R_6$: H; $R_2$, $R_4$, $R_7$: OH; $R_3$: $OCH_3$; X: >C=O; flavone structure

(10) Quercetin
$R_1$, $R_3$, $R_6$: H; $R_2$, $R_4$, $R_5$, $R_7$: OH; X: >C=O; flavone structure

(11) Quercetagetin
$R_1$, $R_6$: H; $R_2$, $R_3$, $R_4$, $R_5$, $R_7$: OH; X: >C=O; flavone structure

(12) Gossypetin
$R_3$, $R_6$: H; $R_1$, $R_2$, $R_4$, $R_5$, $R_7$: OH; X: >C=O; flavone structure

(13) Tricetin
$R_1$, $R_3$, $R_5$: H; $R_2$, $R_4$, $R_6$, $R_7$: OH; X: >C=O; flavone structure

(14) Myricetin
$R_1$, $R_3$: H; $R_2$, $R_4$, $R_5$, $R_6$, $R_7$: OH; X: >C=O; flavone structure

(15) Fisetin
$R_1$, $R_3$, $R_4$, $R_6$: H; $R_2$, $R_5$, $R_7$: OH; X: >C=O; flavone structure

(16) Pinoquercetin
$R_1$, $R_6$: H; $R_2$, $R_4$, $R_5$, $R_7$: OH; $R_3$: $CH_3$; X: >C=O; flavone structure

(17) Pinomyricetin
$R_1$: H; $R_2$, $R_4$, $R_5$, $R_6$, $R_7$: OH; $R_3$: $CH_3$; X: >C=O; flavone structure

(18) Cyanidin
$R_1$, $R_3$, $R_6$: H; $R_2$, $R_4$, $R_5$, $R_7$: OH; X: >$CH_2$; flavylium-ion structure

(19) Delphinidin
$R_1$, $R_3$: H; $R_2$, $R_4$, $R_5$, $R_6$, $R_7$: OH; X: >$CH_2$; flavylium-ion structure

(20) Rutin
$R_1$, $R_3$, $R_6$: H; $R_2$, $R_4$, $R_7$: OH; $R_5$: OR' (R' is β-rutinose); X: >C=O; flavone structure

(21) Quercitrin
$R_1$, $R_3$, $R_6$: H; $R_2$, $R_4$, $R_7$: OH; $R_5$: OR' (R' is α-L-rhamnose); X: >C=O; flavone structure

(22) Isoquercitrin
$R_1$, $R_3$, $R_6$: H; $R_2$, $R_4$, $R_7$: OH; $R_5$: OR' (R' is β-D-glucose); X: >C=O; flavone structure

(23) Hyperin
$R_1$, $R_3$, $R_6$: H; $R_2$, $R_4$, $R_7$: OH; $R_5$: OR' (R' is β-D-galactose); X: >C=O; flavone structure

(24) Avicularin
$R_1$, $R_3$, $R_6$: H; $R_2$, $R_4$, $R_7$: OH; $R_5$: OR' (R' is α-L-arabinose); X: >C=O; flavone structure Other than the above, theaflavin and theaflavin digallate having structures including a flavonoid skeleton; glycosides of the above-identified substances; leucoanthocyanidin; and the like may also be included.

The content of the substance having a flavonoid skeleton relative to the total amount of the reaction solution (A) is preferably 0.1 to 10% by weight, and more preferably 0.5 to 3% by weight. If the content of the substance having a flavonoid skeleton is too small, the hair dyeing effect may be low. If the content of the substance having a flavonoid skeleton is too large, deposition may occur.

The content of benzyl alcohol relative to the total amount of the reaction solution (A) is preferably 0.1 to 10% by weight, and more preferably 0.5 to 4% by weight. If the content of benzyl alcohol is too small, the hair dyeing effect may be low. If the content of benzyl alcohol is too large, unpleasant odor may be strong.

Examples of the thioglycolic acid salt include ammonium thioglycolate, monoethanolamine thioglycolate, sodium thioglycolate, potassium thioglycolate, lithium thioglycolate, and the like.

Among the above, ammonium thioglycolate is used preferably.

The content of the thioglycolic acid salt relative to the total amount of the reaction solution (A) is preferably 0.1 to 30% by weight, and more preferably 2 to 18% by weight. If the content of the thioglycolic acid salt is too small, the hair dyeing effect may be low. If the content of the thioglycolic acid salt is too large, unpleasant odor may be strong.

The temperature of the reaction solution (A) is preferably 25 to 55° C. If the temperature is too low, the hair dyeing effect may be low. If the temperature is too high, one may get burned upon application.

The reaction solution (A) can be obtained by mixing the components.

<Reaction Solution (B)>

The oxidizing agent is preferably selected from a group consisting of a bromate, periodic acid, a periodate, hydrogen peroxide, an inorganic or organic alkali metal peroxide, a peroxy acid salt, an inorganic perhydrate salt, alkyl or aryl peroxide, peroxidase, oxidase, uricase, a percarbonate, a persulfate, and peroxo-monocarbonate.

The hair dye according to the present invention can also be obtained by: adding the substance having a flavonoid skeleton to the reaction solution (A); not adding one type or two or more types selected from benzyl alcohols, and one type or two or more types selected from thioglycolic acid salts; and using a bromate as the oxidizing agent.

Examples of the bromate include sodium bromate, potassium bromate, and the like.

The content of the oxidizing agent relative to the total amount of the reaction solution (B) is preferably 0.5 to 15% by weight, and more preferably 1 to 7.5% by weight. If the content of the oxidizing agent is too small, the hair dyeing effect may be low. If the content of the oxidizing agent is too large, a feel of hair may deteriorate.

Moreover, the reaction (B) of the present invention may be performed under basic conditions.

In particular, it is preferable to add a base when: the substance having a flavonoid skeleton is added to the reaction solution (A); one type or two or more types selected from benzyl alcohols, and one type or two or more types selected from thioglycolic acid salts are not added; and a bromate is used as the oxidizing agent. In this case, it is preferably performed at pH 7 or greater, more preferably pH 8 or greater, and more preferably pH 10 or greater.

When a base is added, pH is adjusted by adding an organic base or inorganic base.

Examples of the organic base include alkanolamines, alkylamines, and the like. Examples of alkanolamines include monoethanolamine, monomethanolamine, isopropanolamine, dimethanolamine, diethanolamine, diisopropanolamine, trimethanolamine, triethanolamine, tripropanolamine, triisopronanolamine, and the like. Examples of alkylamines include methylamine, ethylamine, propylamine, isopropylamine, dimethylamine, diethylamine, dipropylamine, diisopropylamine, trimethylamine, triethylamine, tripropylamine, arginine, lysine, sodium N-methyltaurinate, and the like.

Examples of the inorganic base include sodium hydroxide, potassium hydroxide, ammonia water, and the like.

The base is preferably alkanolamine, more preferably monoethanolamine or diethanolamine, and furthermore preferably monoethanolamine. Moreover, in order to adjust the reaction solution (B) to a suitable basicity, a plurality of bases can be mixed to be used.

The temperature of the reaction solution (B) is preferably 25 to 55° C. If the temperature is too low, the hair dyeing effect may be low. If the temperature is too high, one may get burned upon application.

Moreover, when one type or two or more types selected from benzyl alcohols is/are added to the reaction solution (A), the temperature of the reaction solution (B) is more preferably 25 to 55° C.

When one type or two or more types selected from benzyl alcohols, and one type or two or more types selected from thioglycollic acid salts are not added to the reaction solution (A), and a bromate is used as the oxidizing agent, the temperature of the reaction solution (B) is more preferably 25 to 55° C.

The reaction solution (B) can be obtained by mixing the components.

Other than the above-identified substances, the hair dye according to the present invention can comprise, as necessary, components usually employed in hair dyes. Examples thereof include oily components, higher alcohols, pH adjusters, surfactants, viscosity adjusters, perfumes, stabilizers, drugs, colorants, UV protection agents, water and the like.

Examples of the oily components include: moisturizers such as glycerin, polypropylene glycol, dipropylene glycol, polyethylene glycol, chondroitin sulfate, hyaluronate, diglycerin, 1,3-butylene glycol, pyrrolidonecarboxylic acid salt, sorbitol, maltitol, lactose, oligosaccharide, and the like; shea butter; squalene; lecithin; liquid paraffin; vaseline; higher fatty acids; triglyceride; ester oils; and the like.

Examples of the higher alcohols include: lower alcohols such as ethanol, butanol, propanol, isopropanol, benzyl alcohol, and the like; 2-ethylhexyl alcohol; cetostearyl alcohol; lauryl alcohol; behenyl alcohol; stearyl alcohol; cetyl alcohol; and the like.

Examples of the pH adjusters include salts of alkaline metals such as sodium, potassium, and the like and inorganic acids such as phosphoric acids, sulfuric acids, hydrochloric acids, carbonic acids or organic acids such as citric acids, glycolic acids tartaric acids.

Examples of the nonionic surfactants include: polyoxyethylene-type surfactants such as polyoxyethylene alkyl ether, polyoxyethylene fatty acid ester, polyoxyethylene polyhydric alcohol fatty acid partial ester, polyoxyethylene hydrogenated castor oil derivatives, and the like; alkyl polyglycosides such as octyl polyglycoside, and the like; polyglycerin-type surfactants such as polyglycerin fatty acid ester, polyglycerin alkyl ether, and the like; sugar alcohol hydroxyalkyl ethers such as maltitol hydroxyalkyl ether; fatty acid diethanolamides; and the like.

Moreover, other surfactants including: anionic surfactants such as higher fatty acid salts, alkyl benzene sulfonates, phosphate esters, alkyl sulfate salts, alkyl sulfate ester salts, polyoxyethylene alkyl sulphate ester salts, and the like; and cationic surfactants such as amino acids, alkyltrimethylammonium salt, dialkyldimethylammonium salt, alkyldimethylamine oxide, and the like can also be blended.

The hair dyeing method according to the present invention comprises steps of
  an adsorbing step of immersing hair into a reaction solution (A) comprising: a substance having a flavonoid skeleton represented by the above-identified general formula (1); one type or two or more types selected from benzyl alcohols; and one type or two or more types selected from thioglycolic acid salts; and
  an oxidizing step of immersing the hair into a reaction solution (B) comprising an oxidizing agent.

After a pre-treatment step of immersing hair into a reaction solution (A-1) comprising one type or two or more types selected form benzyl alcohols, and one type or two or more types selected from thioglycolic acid salts, a step of immersing hair into a reaction solution (A-2) comprising a substance having a flavonoid skeleton represented by a general formula (1) can be comprised as the adsorbing step of the reaction solution (A) of the hair dyeing method according to the present invention. The hair dye composition having a high hair dyeing effect can also be obtained by employing this step.

As the adsorbing step of the reaction solution (A), however, hair is preferably immersed into the reaction solution (A) comprising all of the substance having a flavonoid skeleton, one type or two or more types selected form benzyl alcohols, and one type or two or more types selected from thioglycolic acid salts. By comprising this step, the hair dye composition having a higher hair dyeing effect can be obtained.

Moreover, the hair dyeing method according to the present invention comprises steps of:
  an adsorbing step of treating hair with a reaction solution (A) comprising a substance having a flavonoid skeleton represented by the above-identified general formula (1); and
  an oxidizing step of treating the hair with a reaction solution (B) comprising an oxidizing agent consisting of a bromate.

The time required for the absorbing step and the oxidizing step varies by the desired color of dyed hair; however, it is preferably 10 to 60 minutes and 5 to 40 minutes respectively, and more preferably 20 to 40 minutes and 10 to 30 minutes. If the time is too short, the hair dyeing effect may be poor. If the time is too long, improvement in the hair dyeing effect may not be achieved.

EXAMPLES

The present invention will be described with reference to the examples below; however, the present invention is not limited to the following examples. The blending amounts are in "% by weight" relative to the system to which the component is blended, unless otherwise specified.

First, in the hair dye using the substance having a flavonoid skeleton, the substance that can improve hair dyeing effect was examined.

The present inventors manufactured the hair dye (reaction solution (A) and reaction solution (B)) shown in Table 1 below by the following manufacturing method, and performed a hair dyeing test shown below. The color of hair was measured by the following measurement method, and the L-values upon measurement are shown in Table 1 below. It is determined that the lower the value of the L-value is, the darker the hair is dyed.

<Manufacturing Method of the Hair Dye>

The hair dye is manufactured by mixing the components.

<Hair Dyeing Test>

A hair (human white hair, BM-W-A, manufactured by Beaulax Co., Ltd., 0.8 g) was immersed into 100 mL of the reaction solution (A) for 40 minutes at each temperature, and then immersed into the reaction solution (B) similarly. Subsequently, the hair was immersed into 0.1% aqueous solution of sodium polyoxyethylene lauryl sulfate for 20 minutes. Then, the hair was immersed into distilled water for 30 minutes, and dried.

Measurement Method of Dyeability (L-Value of Hair)

Color of a sample was measured with a spectrophotometer (CM-3600d, manufactured by Konica Minolta, Inc.).

$L^*a^*b^*$ color system (CIE1976) was used as the color system. Here, the $L^*$-value in the $L^*a^*b^*$ (L star, a star, b star) color system represents value in a scale that shows brightness relative to color. $a^*$ and $b^*$ together represent chromaticity (hue and chroma). Hue is a scaled attribution of color perception such as red, yellow, green, blue, and the like.

In the Munsell color system, colors are divided into five (R, Y, G, B, P), and YR, GY, BG, PB, and RP are further provided intermediately. These color phases are further divided by 10 to represent 100 color phases in total.

TABLE 1

| | Test Example | 1-1 | 1-2 | 1-3 | 1-4 | 1-5 | 1-6 | 1-7 |
|---|---|---|---|---|---|---|---|---|
| (A) | Tea extract (*1) | — | 3% | 3% | 3% | 3% | 3% | 3% |
| | Benzyl alcohol | — | — | — | — | 4% | 4% | 4% |
| | Ammonium thioglycolate | — | — | — | — | 6% | 6% | 6% |
| | 0.1M acetate buffer (pH 5) | — | Balance | Balance | Balance | Balance | Balance | Balance |
| | pH | — | 5 | 5 | 5 | 5 | 5 | 5 |
| | Temperature | — | 30° C. | 40° C. | 50° C. | 30° C. | 40° C. | 50° C. |
| (B) | Sodium periodate | — | 1% | 1% | 1% | 1% | 1% | 1% |
| | 0.1M phosphate buffer (pH 7) | — | Balance | Balance | Balance | Balance | Balance | Balance |
| | pH | — | 7 | 7 | 7 | 7 | 7 | 7 |
| | Temperature | — | 30° C. | 30° C. | 30° C. | 30° C. | 30° C. | 30° C. |
| | L-value of hair | 72.7 | 53.4 | 52.7 | 46.2 | 42.2 | 29.2 | 30.7 |

(*1): a mixture of: (+)-catechin or (−)-catechin or (+)-epicatechin or (−)-epicatechin; (+)-gallocatechin or (−)-gallocatechin or (−)-epigallocatechin; (−)-catechin gallate or (−)-epicatechin gallate; and (−)-gallocatechin gallate or (−)-epigallocatechin gallate.

From Table 1, it became clear that Text Examples 1-5 to 1-7 to which the tea extract, benzyl alcohol and ammonium thioglycolate were added to the reaction solution (A) had a higher dyeing effect than those to which the above components were not added.

Moreover, it became clear that the dyeing effect was higher when the temperature of the reaction solution (A) was higher.

Next, in the hair dye using the substance having a flavonoid skeleton, timing of adding benzyl alcohol and/or the thioglycolic acid salt was examined.

The present inventors manufactured the hair dye (reaction solution (A) and reaction solution (B)) shown in Table 2 below by the above-identified manufacturing method after performing a pre-treatment by the following method in some cases, and performed the above-identified hair dyeing test. The L-values of hair subjected to the hair dyeing test are shown in Table 2 below.

<Pre-Treatment Method of the Hair Dye>

The hair was immersed into a pre-treatment solution at 30° C. for 40 minutes, and then treated with the reaction solutions (A) and (B).

TABLE 2

| | Test Example | 2-1 | 2-2 | 2-3 | 2-4 | 2-5 |
|---|---|---|---|---|---|---|
| (A) | Pre-treatment | — | 4% BA | 6% ATG | 4% BA + 6% ATG | — |
| | Tea extract (*1) | 3% | 3% | 3% | 3% | 3% |
| | Benzyl alcohol | — | — | — | — | 4% |
| | Ammonium thioglycolate | — | — | — | — | 6% |
| | 0.1M acetate buffer (pH 5) | Balance | Balance | Balance | Balance | Balance |
| | pH | 5 | 5 | 5 | 5 | 5 |
| | Temperature | 30° C. | 30° C. | 30° C. | 30° C. | 30° C. |
| (B) | Sodium periodate | 1% | 1% | 1% | 1% | 1% |
| | 0.1M phosphate buffer (pH 7) | Balance | Balance | Balance | Balance | Balance |
| | L-value of hair | 53.8 | 55.2 | 46.0 | 43.5 | 42.2 |

From Table 2, it became clear that the hair dyeing effect was higher when benzyl alcohol and the thioglycolic acid salt were added together with the tea extract than using them in the pre-treatment phase.

Moreover, it became clear that the hair dyeing effect was higher when both of benzyl alcohol and thioglycolic acid were added than when they were added alone.

Next, the present inventors examined the types of benzyl alcohols (A-2) and ammonium thioglycolates (A-3) that are blended together with the tea extract (A-1).

The results are shown in Table 3.

TABLE 3

| | | Component | 3-1 | 3-2 | 3-3 | 3-4 | 3-5 | 3-6 | 3-7 | 3-8 | 3-9 | 3-10 | 3-11 |
|---|---|---|---|---|---|---|---|---|---|---|---|---|---|
| Reaction solution A | A-1 | Tea extract | 3 | 3 | 3 | 3 | 3 | 3 | 3 | 3 | 3 | 3 | 3 |
| | A-2 | Benzoyl alcohol | — | 4 | — | 4 | — | — | — | 4 | 4 | 4 | 4 |
| | | Propylene carbonate | — | — | — | — | 3.8 | — | — | — | — | — | — |
| | | γ-butyrolactone | — | — | — | — | — | 3.3 | — | — | — | — | — |
| | | Vanillin | — | — | — | — | — | — | 1 | — | — | — | — |
| | A-3 | Ammonium thioglycolate | — | — | 2 | 2 | 2 | 2 | 2 | — | — | — | — |
| | | Cysteamine | — | — | — | — | — | — | — | 2.3 | — | — | — |
| | | Ammonium thiolactate | — | — | — | — | — | — | — | — | '2.3 | — | — |
| | | Cysteamine | — | — | — | — | — | — | — | — | — | 2 | — |
| | | Lactone third | — | — | — | — | — | — | — | — | — | — | 2.3 |
| | Solvent | 0.1M phosphate buffer | Balance | Balance | Balance | Balance | Balance | Balance | Balance | Balance | Balance. | Balance | Balance |
| | | Temperature | 30° C. | 30° C. | 30° C. | 30° C. | 30° C. | 30° C. | 30° C. | 30° C. | 30° C. | 30° C. | 30° C. |
| Reaction solution B | B-1 | Sodium periodate | 1 | 1 | 1 | 1 | 1 | 1 | 1 | 1 | 1 | 1 | 1 |
| | Solvent | 0.1M phosphate buffer (pH 7) | Balance | Balance | Balance | Balance | Balance | Balance | Balance | Balance | Balance | Balance | Balance |
| | | L-value of hair | 51.7 | 47.7 | 49.5 | 42.9 | 46.7 | 47.3 | 47.8 | 42.3 | 45.2 | 31.1 | 50.1 |

From the results shown in Table 3 and other tests, it became clear that vanillin, propylene carbonate, and γ-butyrolactone are used preferably as benzyl alcohols (A-2) other than benzyl alcohol, and a thiolactic acid salt, cysteine, cysteamine and the like are used preferably as thioglycolic acid salts (A-3).

As a result of these examinations carried out by the present inventors, the hair dye according to the present invention consists of the reaction solution (A) comprising: the substance having a flavonoid skeleton represented by the above-identified general formula (1); one type or two or more types selected from benzyl alcohol, vanillin, propylene carbonate, and γ-butyrolactone; and one type or two or more types selected from a thioglycolic acid salt, a thiolactic acid salt, cysteine, and cysteamine, and the reaction solution (B) comprising the oxidizing agent.

Next, in the hair dye using the substance having a flavonoid skeleton, the present inventors examined on a case when a bromate is used as the oxidizing agent of the reaction solution (B).

The present inventors manufactured the hair dye (reaction solution (A) and reaction solution (B)) shown in Table 4 below by the above-identified manufacturing method, and performed the above-identified hair dyeing test. The L-values of the hair subjected to the hair dyeing test are shown in Table 4 below.

TABLE 4

| | Test Example | 1-1 | 4-1 | 4-2 | 4-3 | 4-4 | 4-5 |
|---|---|---|---|---|---|---|---|
| (A) | Tea extract (*1) | — | 3% | 3% | 3% | 3% | 3% |
| | 0.1M acetate buffer (pH 5) | — | Balance | Balance | Balance | Balance | Balance |
| | pH | — | 5 | 5 | 5 | 5 | 5 |
| | Temperature | — | 50° C. | 50° C. | 50° C. | 50° C. | 50° C. |
| (B) | Sodium bromate | — | 7.50% | 7.50% | 15% | 30% | — |
| | Monoethanolamine | — | 6.10% | 6.10% | 6.10% | 6.10% | 6.10% |
| | Purified water | — | Balance | Balance | Balance | Balance | Balance |
| | pH | — | 12 | 12 | 12 | 12 | 12 |
| | Temperature | — | 30° C. | 50° C. | 50° C. | 50° C. | 50° C. |
| | L-value of hair | 72.7 | 53.8 | 55 | 53.9 | 53.8 | 62.5 |

From Table 4, the hair dye composition having a high hair dyeing effect could be obtained by using the bromate as the oxidizing agent without using benzyl alcohol and the thioglycolic acid salt.

Accordingly, the hair dye according to the present invention consists of the reaction solution (A) comprising the substance having a flavonoid skeleton represented by the above-identified general formula (1), and the reaction solution (B) comprising an oxidizing agent consisting of the bromate.

Next, in the hair dye using the substance having a flavonoid skeleton, pH of the reaction solution (B) was examined when the bromate was used as the oxidizing agent of the reaction solution (B).

The present inventors manufactured the hair dye (reaction solution (A) and reaction solution (B)) shown in Table 5 below by the above-identified manufacturing method, and performed the above-identified hair dyeing test. The L-values of the hair subjected to the hair dyeing test are shown in Table 5.

TABLE 5

| Test Example | 5-1 | 5-2 | 5-3 | 5-4 | 5-5 | 5-6 |
|---|---|---|---|---|---|---|
| (A) Tea extract (*1) | — | 3% | 3% | 3% | 3% | 3% |
| Acrylic acid/acrylamidomethyl propane sulfonic acid copolymer | — | 1% | 1% | 1% | 1% | 1% |
| Phenoxyethanol | — | 0.50% | 0.50% | 0.50% | 0.50% | 0.50% |
| Purified water | — | Balance | Balance | Balance | Balance | Balance |
| pH | — | 4 | 4 | 4 | 4 | 4 |
| Temperature | — | 40° C. | 40° C. | 40° C. | 40° C. | 40° C. |
| (B) Sodium bromate | — | 7.50% | 7.50% | 7.50% | 7.50% | 7.50% |
| Sodium periodate | — | — | — | — | — | — |
| Monoethanolamine | — | 2.50% | 3% | 4% | 5% | 6.10% |
| 2M phosphate buffer (pH 6) | — | Balance | Balance | Balance | Balance | — |
| Purified water | — | — | — | — | — | Balance |
| pH | — | 7 | 8 | 9 | 10 | 11 |
| Temperature | — | 40° C. | 40° C. | 40° C. | 40° C. | 40° C. |
| L-value of hair | 63.4 | 39.2 | 38.6 | 36 | 32.9 | 31.9 |

From Table 5, it became clear that, when the bromate was used as the oxidizing agent of the reaction solution (B), the hair dyeing effect became higher as pH of the reaction solution (B) was increased.

Accordingly, when the bromate is used as the oxidizing agent according to the present invention, pH of the reaction solution (B) is preferably 7 or greater.

Next, the present inventors tested, by a dyeability measurement method shown below, the hair dyed with the hair dye using sodium periodate as the oxidizing agent of the reaction solution (B) shown in Test Example 6-7, and the hair dyed with the hair dye using sodium bromate as the oxidizing agent of the reaction solution (B) shown in the Test Example 6-6 by the following hair dyeing method. The results of color measurement are shown in Table 6.

<Hair Dyeing Method>

1 g of a test composition (A) was applied to a hair (human hair, BR-3-A, manufactured by manufactured by Beaulax Co., Ltd., 3 g), and the hair was left at a constant temperature for a fixed period of time. After washing the hair with running water, 1 g of a test composition (B) was applied to the hair, and the hair was left at a constant temperature for a fixed period of time. Then, the hair was washed with running water, and dried.

TABLE 6

| Test Example | 6-1 | 6-2 | 6-3 | 6-4 | 6-5 | 6-6 | 6-7 |
|---|---|---|---|---|---|---|---|
| (A) Tea extract (*1) | — | 3% | 3% | 3% | 3% | 3% | 3% |
| Acrylic acid/acrylamidomethyl propane sulfonic acid copolymer | — | 1% | 1% | 1% | 1% | 1% | 1% |
| Phenoxyethanol | — | 0.50% | 0.50% | 0.50% | 0.50% | 0.50% | 0.50% |
| Purified water | — | Balance | Balance | Balance | Balance | Balance | Balance |
| pH | — | 4 | 4 | 4 | 4 | 4 | 4 |
| Temperature | — | 40° C. | 40° C. | 40° C. | 40° C. | 40° C. | 40° C. |
| (B) Sodium bromate | — | 7.50% | 7.50% | 7.50% | 7.50% | 7.50% | — |
| Sodium periodate | — | — | — | — | — | — | 1.00% |
| Monoethanolamine | — | 2% | 3% | 4% | 5% | 6.10% | 6.10% |
| 2M phosphate buffer (pH 6) | — | Balance | Balance | Balance | Balance | — | — |
| Purified water | — | — | — | — | — | Balance | Balance |
| pH | — | 7 | 8 | 9 | 10 | 11 | 11 |
| Temperature | — | 40° C. | 40° C. | 40° C. | 40° C. | 40° C. | 40° C. |
| L-value of hair | 63.4 | 40.8 | 38.6 | 36 | 32.9 | 31.9 | 29 |

TABLE 6-continued

| Test Example | 6-1 | 6-2 | 6-3 | 6-4 | 6-5 | 6-6 | 6-7 |
|---|---|---|---|---|---|---|---|
| Δa from untreated hair | — | 3.4 | 4.1 | 5.1 | 5.4 | 5.2 | 1.5 |
| Δb from untreated hair | — | −16.2 | −16.1 | −15.4 | −16.1 | −16.3 | −14.9 |
| Munsell color system | 1.2Y | 4.4YR | 4.0YR | 3.8YR | 3.4YR | 3.4YR | 7.4YR |

From Test Example 6-6 and Test Example 6-7 of Table 6, the L-value of the hair dyed with sodium bromate is almost the same as the hair dyed with sodium periodate; however, Δa and Δb values from untreated hair are greater in the hair dyed with sodium bromate, and Munsell color system greatly differs too. That is, the change of color from the original hair bundle (bleached hair) is greater. Color variation can be enjoyed, and a highly fashionable dyeability can be achieved with sodium bromate than sodium periodate.

Next, the present inventors immersed the hair dyed with Test Example 6-6 and Test Example 6-7 into an activator (sodium polyoxyethylene lauryl ether sulfate) solution at 40° C. for 30 minutes to perform a discoloration treatment. Then, the present inventors tested the hair by the above-identified dyeability measurement method. The results are shown in Table 7.

TABLE 7

| Test Example | ΔE |
|---|---|
| 6-6 (sodium bromate) | 0.4 |
| 6-7 (sodium periodate) | 1.3 |

From Table 7, it became clear that, with respect to the color after the discoloration treatment, the ΔE value was 0.9 points lower in sodium bromate, and dyeability was maintained than sodium periodate.

Hereinbelow, formulation examples of the hair dye according to the present invention are given. It is needless to say that the present invention is not limited to these formulation examples, and the present invention is specified by the scope of claims.

Formulation Example 1 of Reaction Solution (A)

| Formulation Example of Reaction solution (A) | A-1 | A-2 | A-3 | A-4 | A-5 |
|---|---|---|---|---|---|
| Tea extract (*1) | 3.00 | 3.00 | 3.00 | 3.00 | 3.00 |
| Stearyl alcohol | 5.00 | — | — | — | — |
| Cetanol | 2.00 | — | — | — | — |
| Stearyltrimethylammonium chloride | 1.50 | — | — | — | — |
| Polyoxyethylene cetyl ether (40E.O) | 1.50 | — | — | — | — |
| Liquid paraffin | 0.50 | — | — | — | — |
| Hydroxyethyl cellulose | — | 1.00 | — | — | — |
| Xanthan gum | — | — | 1.00 | — | — |
| Acrylates/C10-30 alkyl acrylate crosspolymer | — | — | — | 0.50 | — |
| Acrylic acid/acrylamidomethyl propane sulfonic acid copolymer | — | — | — | — | 0.50 |
| Phenoxyethanol | 0.50 | 0.50 | 0.50 | 0.50 | 0.50 |
| Disodium hydrogen phosphate | Suitable amount | Suitable amount | Suitable amount | Suitable amount | Suitable amount |
| Sodium dihydrogen phosphate | Suitable amount | Suitable amount | Suitable amount | Suitable amount | Suitable amount |
| Sodium hydroxide (pH adjuster) | — | — | — | Suitable amount | Suitable amount |
| Purified water | Balance | Balance | Balance | Balance | Balance |
| pH | 5.0 | 5.0 | 5.0 | 5.0 | 5.0 |

Formulation Example 2 of Reaction Solution (A)

| Formulation Example of Reaction solution (A) | A-6 | A-7 | A-8 | A-9 | A-10 | A-11 | A-12 | A-13 | A-14 |
|---|---|---|---|---|---|---|---|---|---|
| Tea extract (*1) | 3.00 | 3.00 | 3.00 | 3.00 | 3.00 | 3.00 | 3.00 | 3.00 | 3.00 |
| Stearyl alcohol | 5.00 | 5.00 | 5.00 | 5.00 | 5.00 | — | — | — | — |
| Cetanol | 2.00 | 2.00 | 2.00 | 2.00 | 2.00 | — | — | — | — |
| Stearyltrimethylammonium chloride | 1.50 | 1.50 | 1.50 | 1.50 | 1.50 | — | — | — | — |
| Polyoxyethylene cetyl ether (40E.O) | 1.50 | 1.50 | 1.50 | 1.50 | 1.50 | — | — | — | — |
| Liquid paraffin | 0.50 | 0.50 | 0.50 | 0.50 | 0.50 | — | — | — | — |
| Hydroxyethyl cellulose | — | — | — | — | — | 1.00 | — | — | — |

-continued

| | Formulation Example of Reaction solution (A) | | | | | | | | |
|---|---|---|---|---|---|---|---|---|---|
| | A-6 | A-7 | A-8 | A-9 | A-10 | A-11 | A-12 | A-13 | A-14 |
| Xanthan gum | — | — | — | — | — | — | 1.00 | — | — |
| Acrylates/C10-30 alkyl acrylate crosspolymer | — | — | — | — | — | — | — | 0.50 | — |
| Acrylic acid/acrylamidomethyl propane sulfonic acid copolymer | — | — | — | — | — | — | — | — | 0.50 |
| Benzyl alcohol | 4.00 | 4.00 | 4.00 | 4.00 | 4.00 | 4.00 | 4.00 | 4.00 | 4.00 |
| Ammonium thioglycolate | 2.00 | 4.00 | 6.00 | 6.00 | 6.00 | 6.00 | 6.00 | 6.00 | 6.00 |
| Phenoxyethanol | 0.50 | 0.50 | 0.50 | 0.50 | 0.50 | 0.50 | 0.50 | 0.50 | 0.50 |
| Disodium hydrogen phosphate | Suitable amount | Suitable amount | Suitable amount | Suitable amount | Suitable amount | Suitable amount | Suitable amount | Suitable amount | Suitable amount |
| Sodium dihydrogen phosphate | Suitable amount | Suitable amount | Suitable amount | Suitable amount | Suitable amount | Suitable amount | Suitable amount | Suitable amount | Suitable amount |
| Sodium hydroxide (pH adjuster) | — | — | — | — | — | — | — | Suitable amount | Suitable amount |
| Purified water | Balance | Balance | Balance | Balance | Balance | Balance | Balance | Balance | Balance |
| pH | 5.4 | 5.4 | 5.4 | 5.7 | 6.5 | 5.4 | 5.4 | 5.4 | 5.4 |

Formulation Example 1 of Reaction Solution (B)

| | Formulation Example of Reaction solution (B) | | | | | | |
|---|---|---|---|---|---|---|---|
| | B-1 | B-2 | B-3 | B-4 | B-5 | B-6 | B-7 |
| Sodium bromate | 7.50 | 7.50 | 15.00 | 7.50 | 7.50 | 7.50 | 7.50 |
| Stearyl alcohol | 5.00 | 5.00 | 5.00 | — | — | — | — |
| Cetanol | 2.00 | 2.00 | 2.00 | — | — | — | — |
| Stearyltrimethylammonium chloride | 1.50 | 1.50 | 1.50 | — | — | — | — |
| Polyoxyethylene cetyl ether (40E.O) | 1.50 | 1.50 | 1.50 | — | — | — | — |
| Liquid paraffin | 0.50 | 0.50 | 0.50 | — | — | — | — |
| Hydroxyethyl cellulose | — | — | — | 1.00 | — | — | — |
| Xanthan gum | — | — | — | — | 1.00 | — | — |
| Acrylates/C10-30 alkyl acrylate crosspolymer | — | — | — | — | — | 0.50 | — |
| Acrylic acid/acrylamidomethyl propane sulfonic acid copolymer | — | — | — | — | — | — | 0.50 |
| Monoethanolamine | Suitable amount | Suitable amount | Suitable amount | Suitable amount | Suitable amount | Suitable amount | Suitable amount |
| Purified water | Balance | Balance | Balance | Balance | Balance | Balance | Balance |
| pH | 11.7 | 12.2 | 12.2 | 11.7 | 11.7 | 11.7 | 11.7 |

The invention claimed is:

1. A hair dye consisting of:
a reaction solution (A) comprising: a substance having a specific flavonoid skeleton represented by a general formula (1) below; one type or two or more types selected from benzyl alcohol, vanillin, propylene carbonate, and γ-butyrolactone; and one type or two or more types selected from a thioglycolic acid salt, a thiolactic acid salt, cysteine and cysteamine, and
a reaction solution (B) comprising an oxidizing agent,

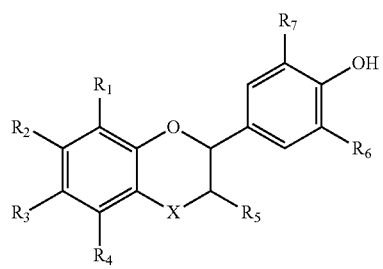

(1)

wherein: $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents $>CH_2$, $>C=O$, or $>CHOH$.

2. A hair dye consisting of:
a reaction solution (A) comprising a substance having a flavonoid skeleton represented by the general formula (1), and
a reaction solution (B) comprising an oxidizing agent consisting of a bromate,

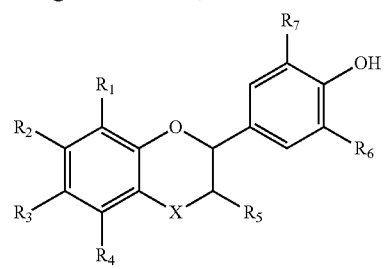

(1)

wherein: $R_1$, $R_2$, $R_3$, $R_4$, $R_6$, and $R_7$ independently represent a hydrogen atom, a hydroxy group, or a methyl group; either one or both of $R_6$ and $R_7$ is/are a hydroxy group; $R_5$ represents a hydrogen atom, a hydroxy group, a galloyl group, or a saccharide; and X represents >$CH_2$, >C=O, or >CHOH.

3. The hair dye according to claim 1, wherein the oxidizing agent is selected from a group consisting of a bromate, periodic acid, a periodate, hydrogen peroxide, an inorganic or organic alkali metal peroxide, a peroxy acid salt, an inorganic perhydrate salt, alkyl or aryl peroxide, peroxidase, oxidase, uricase, a percarbonate, a persulfate, and peroxomonocarbonate.

4. The hair dye according to claim 2, wherein pH of the reaction solution (B) is 7 or greater.

5. A hair dyeing method comprising steps of:
an adsorbing step of treating hair with a reaction solution (A) comprising: a substance having a flavonoid skeleton represented by the general formula (1); one type or two or more types selected from benzyl alcohol, vanillin, propylene carbonate, and γ-butyrolactone; and one type or two or more types selected from a thioglycolic acid salt, a thiolactic acid salt, cysteine and cysteamine; and
an oxidizing step of treating the hair with a reaction solution (B) comprising an oxidizing agent,

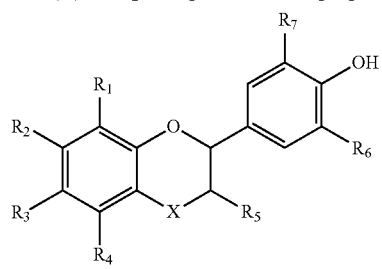

(1)

wherein: $R_1$, $R_2$, $R_3$, $R_4$, $R_6$, and $R_7$ independently represent a hydrogen atom, a hydroxy group, or a methyl group; either one or both of $R_6$ and $R_7$ are a hydroxy group; $R_5$ represents a hydrogen atom, a hydroxy group, a galloyl group, or a saccharide; and X represents >$CH_2$, >C=O, or >CHOH.

6. A hair dyeing method comprising steps of:
an adsorbing step of treating hair with a reaction solution (A) comprising a substance having a flavonoid skeleton represented by the general formula (1); and
an oxidizing step of treating the hair with a reaction solution (B) comprising an oxidizing agent consisting of a bromate,

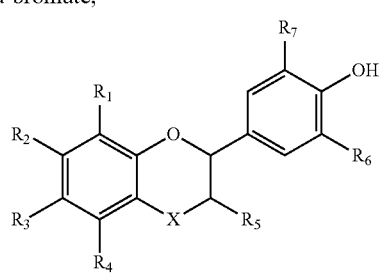

(1)

wherein: $R_1$, $R_2$, $R_3$, $R_4$, $R_6$, and $R_7$ independently represent a hydrogen atom, a hydroxy group or a methyl group; either one or both of $R_6$ and $R_7$ are a hydroxy group; $R_5$ represents a hydrogen atom, a hydroxy group, a galloyl group, or a saccharide; and X represents >$CH_2$, >C=O or >CHOH.

7. The hair dyeing method according to claim 5, wherein the oxidizing agent is selected from a group consisting of a bromate, periodic acid, a periodate, hydrogen peroxide, inorganic or organic alkali metal peroxide, a peroxy acid salt, an inorganic perhydrate salt, alkyl or aryl peroxide, peroxidase, oxidase, uricase, a percarbonate, a persulfate, and peroxo monocarbonate.

8. The hair dyeing method according to claim 6, wherein pH of the reaction solution (B) is 7 or greater.

9. A hair dyeing method comprising steps of:
an adsorbing step of treating hair with a reaction solution (A-2) comprising a substance having a flavonoid skeleton represented by the general formula (1) after a pre-treatment step of treating hair with a reaction solution (A-1) comprising: one type or two or more types selected form benzyl alcohol, vanillin, propylene carbonate, and γ-butyrolactone; and one type or two or more types selected from a thioglycolic acid salt, a thiolactic acid salt, cysteine and cysteamine; and
an oxidizing step of treating the hair with a reaction solution (B) comprising an oxidizing agent,

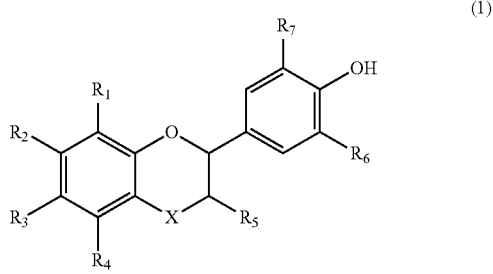

(1)

wherein: $R_1$, $R_2$, $R_3$, $R_4$, $R_6$, and $R_7$ independently represent a hydrogen atom, a hydroxy group, or a methyl group; either one or both of $R_6$ and $R_7$ are a hydroxy group; $R_5$ represents a hydrogen atom, a hydroxy group, a galloyl group, or a saccharide; and X represents >$CH_2$, >C=O, or >CHOH.

10. The hair dyeing method according to claim 9, wherein the oxidizing agent is selected from a group consisting of a bromate, periodic acid, a periodate, hydrogen peroxide, inorganic or organic alkali metal peroxide, a peroxy acid salt, an inorganic perhydrate salt, alkyl or aryl peroxide, peroxidase, oxidase, uricase, a percarbonate, a persulfate, and peroxo monocarbonate.

* * * * *